United States Patent
Neuba et al.

(10) Patent No.: US 10,376,454 B2
(45) Date of Patent: *Aug. 13, 2019

(54) PRODUCTS FOR THE OXIDATIVE DYEING OF HAIR IN COPPER SHADES WITH IMPROVED GRAY COVERAGE

(71) Applicant: Henkel AG & Co. KGaA, Duesseldorf (DE)

(72) Inventors: Constanze Neuba, Grevenbroich (DE); Burkhard Mueller, Duesseldorf (DE)

(73) Assignee: Henkel AG & Co. KGaA, Dusseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/578,289

(22) PCT Filed: May 31, 2016

(86) PCT No.: PCT/EP2016/062232
§ 371 (c)(1),
(2) Date: Nov. 30, 2017

(87) PCT Pub. No.: WO2017/001132
PCT Pub. Date: Jan. 5, 2017

(65) Prior Publication Data
US 2018/0140524 A1    May 24, 2018

(30) Foreign Application Priority Data
Jun. 29, 2015  (DE) .................. 10 2015 212 003

(51) Int. Cl.
*A61Q 5/10*   (2006.01)
*A61K 8/49*   (2006.01)
*A61K 8/41*   (2006.01)
*A61Q 5/06*   (2006.01)

(52) U.S. Cl.
CPC ............. *A61K 8/494* (2013.01); *A61K 8/411* (2013.01); *A61K 8/415* (2013.01); *A61K 8/4926* (2013.01); *A61Q 5/065* (2013.01); *A61Q 5/10* (2013.01); *A61K 2800/88* (2013.01)

(58) Field of Classification Search
CPC .......... A61Q 5/10; A61Q 5/065; A61K 8/411; A61K 8/415; A61K 8/4926; A61K 8/494; A61K 2800/88
See application file for complete search history.

(56) References Cited

U.S. PATENT DOCUMENTS

| | | | |
|---|---|---|---|
| 8,740,995 B1 * | 6/2014 | Schweinsberg | A61K 8/4926 132/202 |
| 9,655,827 B2 * | 5/2017 | Gebert-Schwarzwaelder | A61K 8/34 |
| 2016/0263002 A1 | 9/2016 | Gebert-Schwarzwaelder et al. | |
| 2016/0263004 A1 | 9/2016 | Gebert-Schwarzwaelder et al. | |
| 2016/0263406 A1 | 9/2016 | Gebert-Schwarzwaelder et al. | |

FOREIGN PATENT DOCUMENTS

DE    602004003290 T2    12/2004

OTHER PUBLICATIONS

EPO, International Search Report and Written Opinion issued in International Application No. PCT/EP2016/062232, dated Sep. 20, 2016.

* cited by examiner

*Primary Examiner* — Eisa B Elhilo
(74) *Attorney, Agent, or Firm* — Lorenz & Kopf, LLP

(57) ABSTRACT

Agent for the oxidative dyeing of keratinous fibers is provided herein. The agent includes in a cosmetic carrier (A) 1-(2-Hydroxyethyl)-4,5-diaminopyrazole and/or one of the physiologically-tolerated salts thereof. The agent further includes (B) 2,6-dihydroxy-3,4-dimethylpyridine. The agent also includes (C) p-phenylendiamine, toluene-2,5-diamine, 2-(2,5-diaminophenyl)ethanol and/or one of the physiologically-tolerated salts thereof.

16 Claims, No Drawings

PRODUCTS FOR THE OXIDATIVE DYEING OF HAIR IN COPPER SHADES WITH IMPROVED GRAY COVERAGE

CROSS-REFERENCE TO RELATED APPLICATION

This application is a U.S. National-Stage entry under 35 U.S.C. § 371 based on International Application No. PCT/EP2016/062232, filed May 31, 2016 which was published under PCT Article 21(2) and which claims priority to German Application No. 10 2015 212 003.1, filed Jun. 29, 2015, which are all hereby incorporated in their entirety by reference.

TECHNICAL FIELD

The subject matter of the present disclosure is an agent for the oxidative dyeing of keratinous fibers, more particularly human hair, which contains a special combination of oxidation dye precursors. The agent as contemplated herein contains, in a cosmetic carrier (A), the developer 1-(2-hydroxyethyl)-4,5-diaminopyrazole and/or a physiologically tolerated salt thereof, (B) the coupler 2,6-dihydroxy-3,4-dimethylpyridine and (C), at least one developer from the group of p-phenylendiamine, toluene-2,5-diamine, 2-(2,5-diaminophenyl)ethanol and/or a physiologically tolerated salt thereof. A second subject matter of the present disclosure is a method for the dyeing of keratinous fibers, wherein the aforementioned agent is mixed with an oxidant and applied to the keratin fibers.

Changing the color of keratinous fibers, more particularly of hair, constitutes an important area of modern cosmetics. Consequently, the hair's appearance can be adapted both to current fashion trends and also to the particular preferences of each and every person. Various possibilities of changing the color of hair are known to a person skilled in the art. The color of hair can be changed temporarily by employing partially-oxidizing dyes. In this process, dyes already formed diffuse from the colorant into the hair fibers. Dyeing with partially-oxidizing dyes causes less hair damage. The disadvantage, however, is that the colors achieved with partially-oxidizing dyes have a low permanency and can be washed out quickly.

If the consumer wants a long-lasting color result or a tint which is lighter than the original hair color, oxidative colorants are normally used. To achieve permanent, intense colors with corresponding fastness properties, so-called oxidative colorants are used. Such colorants usually contain oxidation dye precursors, so-called developer components and coupler components, which form the dyes per se under the influence of oxidants. Oxidative colorants are exemplified by long-lasting color results.

Extensive prior art exists for oxidative colorants. Numerous tests have already been carried out, particularly for optimizing fastness properties and for achieving the highest possible degree of gray coverage.

Despite the high number of optimization tests already carried out, however, there is still room for improvement with respect to the gray coverage of oxidatively dyed keratin fibers—more particularly when said fibers are to be dyed with fashionable reddish tints. Above all, the fastness properties and gray coverage of red-violet and bright copper tints cannot yet be categorized as optimal.

The present disclosure therefore addressed the problem of providing oxidative dyes for achieving bright copper tints with improved fastness properties and improved gray coverage. Essentially, the present disclosure addressed the problem of improving fastness to washing and gray coverage on partially graying hair.

The fastness to washing of a color tint means the color change of the hair strands colored by employing said tints under the influence of multiple hair washes. Said color change can relate to both a color shift in the direction of a different shade and also to the fading of the coloration. Neither color change is desired by the user. Tints with good fastness to washing do not change color or barely change color even after repeated hair washes. The hair can be washed by employing a shampoo, a conditioning shampoo or also a conditioner.

The gray coverage of a tint means the ability of said tint to produce a uniform color result on partially graying hair (i.e. on hair which still has from about 30 to about 70% of its original color intact, a significant proportion of said hair, however, having grayed). Once a colorant with good gray coverage has been applied, the visible color differences are minimal, and therefore the grayed hair is barely distinguishable from the pigmented hair after the dyeing process.

BRIEF SUMMARY

Agent for the oxidative dyeing of keratinous fibers is provided herein. The agent includes in a cosmetic carrier (A) 1-(2-Hydroxyethyl)-4,5-diaminopyrazole and/or one of the physiologically-tolerated salts thereof. The agent further includes (B) 2,6-dihydroxy-3,4-dimethylpyridine. The agent also includes (C) p-phenylendiamine, toluene-2,5-diamine, 2-(2,5-diaminophenyl)ethanol and/or one of the physiologically-tolerated salts thereof.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

It has now emerged that keratinous fibers can be dyed in bright copper shades if a special combination of (A) the developer 1-(2-hydroxyethyl)-4,5-diaminopyrazole, (B) the coupler 2,6-dihydroxy-3,4-dimethylpyridine and (C) a developer from the group of p-phenylendiamine, toluene-2, 5-diamine, 2-(2,5-diaminophenyl)ethanol is used in the dyes. Unexpectedly, these agents are exemplified by a gray coverage which is far superior to the formulations known from the prior art.

A first subject matter of the present disclosure is an agent for the oxidative dyeing of keratinous fibers, containing in a cosmetic carrier
(A) 1-(2-Hydroxyethyl)-4,5-diaminopyrazole and/or one of the physiologically-tolerated salts thereof and
(B) 2,6-dihydroxy-3,4-dimethylpyridine and
(C) p-phenylendiamine, toluene-2,5-diamine, 2-(2,5-diaminophenyl)ethanol and/or one of the physiologically-tolerated salts thereof.

Keratinous fibers, keratin-containing fibers or keratin fibers are furs, wool, feathers and, in particular, human hair. Although the agents as contemplated herein are most suitable for lightening and coloring keratin fibers, they can in principle be used for other purposes.

A first subject matter of the present disclosure is an agent for the oxidative dyeing of human hair, containing in a cosmetic carrier (A) 1-(2-Hydroxyethyl)-4,5-diaminopyrazole and/or one of the physiologically-tolerated salts thereof and (B) 2,6-dihydroxy-3,4-dimethylpyridine and (C) p-phenylendiamine, toluene-2,5-diamine, 2-(2,5-diaminophenyl)ethanol and/or one of the physiologically-tolerated salts thereof.

The agents contain the oxidation dye precursors as contemplated herein from the Groups (A), (B) and (C) in a cosmetic carrier, preferably in a suitable aqueous, alcoholic or aqueous alcoholic carrier. Carriers such as creams, emulsions, gels or tenside-containing, foaming solutions, such as shampoos, foaming aerosols, foam formulations or other preparations suitable for application on the hair, are used for oxidative dyeing. Agents for oxidative dyeing of keratinous fibers are most preferably creams or emulsions.

The agent as contemplated herein is exemplified by its content of oxidation dye precursors of developer types (A) and (C), as well as its content of oxidation dye precursors of coupler type (B).

A developer according to the present disclosure is an oxidation dye precursor of the developer type. A coupler according to the present disclosure is an oxidation dye precursor of the coupler type.

As a first oxidation dye precursor of developer type (A), the agents as contemplated herein contain 4,5-diamino-1-(2-hydroxyethyl)-1H-pyrazole and/or one of the physiologically-tolerated salts thereof.

The prior art essentially discloses that 4,5-diamino-1-(2-hydroxyethyl)-1H-pyrazole (A) has a good suitability for producing fashionable tints in the red, violet and copper range. It was not known, however, that when developer (A) 4,5-diamino-1-(2-hydroxyethyl)-1H-pyrazole is mixed with the special coupler (B) described below and a further developer (C) (and also where applicable a second coupler (D)), bright copper shades are more particularly obtained, the fastness to washing and gray coverage of which are far superior to the mixtures known from the prior art.

4,5-diamino-1-(2-hydroxyethyl)-1H-pyrazole is a compound of the Formula (I).

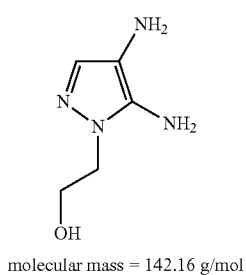

molecular mass = 142.16 g/mol

Preferred physiologically-tolerated salts of 4.5-diamino-1-(2-hydroxyethyl)-1H-pyrazole are preferably hydrochlorides (monohydrochloride×HCl, or dihydrochloride×2 HCl), sulfate (×H$_2$SO$_4$) and hydrobromides (monohydrobromide× HBr, or dihydrobromide×2 HBr) of the compound. Most preferred is 4,5-diamino-1-(2-hydroxyethyl)-1H-pyrazole sulfate (Formula (Ia)).

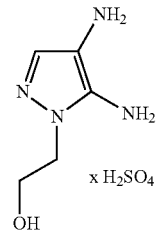

molecular mass = 240.23 g/mol

As a second oxidation dye precursor of the coupler type as contemplated herein, the agents (B) as contemplated herein contain 2,6-dihydroxy-3,4-dimethylpyridine. 2,6-dihydroxy-3,4-dimethylpyridine is a heterocyclic dihydroxy compound of the Formula (II).

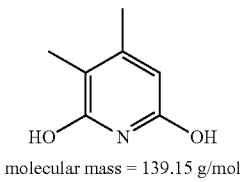

molecular mass = 139.15 g/mol 2,6-dihydroxy-3,4-dimethylpyridine (B) is preferably used in the form of its free compound.

As a third oxidation dye precursor as contemplated herein and/or as a third group of oxidation dye precursors, the agent (C) as contemplated herein contains at least one compound from the group of p-phenylendiamine, toluene-2,5-diamine, 2-(2,5-diaminophenyl)ethanol and/or the physiologically compatible salts of said compounds.

p-phenylendiamine is a compound of the Formula (III). Toluene-2,5-diamine (alternative name: p-toluylendiamine, 2-methyl-p-phenylediamine) is a compound of the Formula (IV).

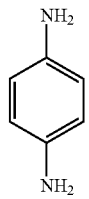

molecular mass = 108.14 g/mol

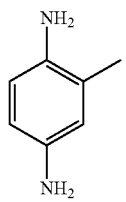

molecular mass = 122.17 g/mol 2-(2,5-diaminophenyl)ethanol is a compound of the Formula (V).

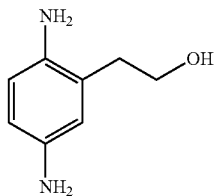

molecular mass = 152.20 g/mol

Preferred physiologically-tolerated salts of p-phenylendiamine are preferably hydrochlorides (monohydrochloride×HCl, or dihydrochloride×2 HCl), sulfate (×H$_2$SO$_4$) and hydrobromides (monohydrobromide×HBr, or dihydrobromide×2 HBr) of the compound.

Preferred physiologically-tolerated salts of toluene-2,5-diamine are preferably hydrochlorides (monohydrochloride×HCl, or dihydrochloride×2 HCl), sulfate (×H$_2$SO$_4$) and hydrobromides (monohydrobromide×HBr, or dihydrobromide×2 HBr) of the compound. Toluene-2,5-diamine sulfate (Formula (IVa)) is most preferred.

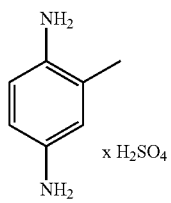

molecular mass = 220.392 g/mol

Preferred physiologically-tolerated salts of 2-(2,5-diaminophenyl)ethanol are preferably hydrochlorides (monohydrochloride×HCl, or dihydrochloride×2 HCl), sulfate (×H$_2$SO$_4$) and hydrobromides (monohydrobromide×HBr, or dihydrobromide×2 HBr) of the compound. 2-(2,5-diaminophenyl)ethanol sulfate (Formula (Va)) is most preferred.

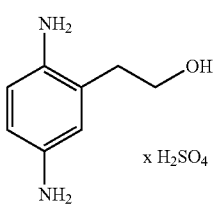

molecular mass = 250.27 g/mol

The tests that led to this present disclosure have shown that adding one or more developers from the group (C) to form the combination of 1-(2-hydroxyethyl)-4,5-diaminopyrazole (A) and 2,6-dihydroxy-3,4-dimethylpyridine (B) permits the development of bright copper tints, which are exemplified by a significant improvement in gray coverage.

Toluene-2,5-diamine and/or one of the physiologically-tolerated salts thereof has proven highly suitable in this regard. In a particularly preferred embodiment, an agent as contemplated herein contains toluene-2,5-diamine and/or one of the physiologically-tolerated salts thereof.

In other words, an agent as contemplated herein in a particularly preferred embodiment contains (C) toluen-2,5-diamine, toluene-2,5-diamine monohydrochloride, toluene-2,5-diamine dihydrochloride, toluene-2,5-diamine monohydrobromide, toluene-2,5-diamine dihydrobromide and/or toluene-2,5-diamine sulfate.

In a most preferred embodiment, an agent as contemplated herein contains toluene-2,5-diamine sulfate.

The gray coverage of the copper tint was also significantly improved by adding the developer (C) 2-(2,5-diaminophenyl)ethanol and/or one of the physiologically-tolerated salts thereof to form the combination of (A) and (B).

In another particularly preferred embodiment, an agent as contemplated herein contains 2-(2,5-diaminophenyl)ethanol and/or one of the physiologically-tolerated salts thereof.

In other words, an agent as contemplated herein in another particularly preferred embodiment contains 2-(2,5-diaminophenyl)ethanol, 2-(2,5-di aminophenyl)ethanol monohydrochloride, 2-(2,5-diaminophenyl)ethanol dihydrochloride, 2-(2,5-diaminophenyl)ethanol monohydrobromide, 2-(2,5-diaminophenyl)ethanol dihydrobromide and/or 2-(2,5-diaminophenyl)ethanol sulfate.

In a most preferred embodiment, an agent as contemplated herein contains 2-(2,5-diaminophenyl)ethanol sulfate.

In order to obtain brilliant copper tints, which have optimal properties with respect both fastness and gray coverage, the use of the essential oxidation dye precursors (A), (B) and (C) in highly-specific quantities is particularly advantageous.

1-(2-hydroxyethyl)-4,5-diaminopyrazole (A) and/or one of the physiologically-tolerated salts thereof can be used in a quantity range from about 0.005 to about 5.0 wt. %—relative to the total weight of the agent as contemplated herein.

The best gray coverage—even when optimally minimizing skin coloration at the same time—is obtained herein, when 1-(2-hydroxyethyl)-4,5-diaminopyrazole sulfate is used in the agent as contemplated herein in a quantity range from about 0.05 to about 3.0 wt. %, more preferably from about 0.1 to about 2.5 wt. %, even more preferably from about 0.3 to about 2.0 wt. % and most preferably from about 0.4 to about 0.9 wt. % (relative to the total weight of the agent as contemplated herein).

In a particularly preferred embodiment, an agent as contemplated herein contains—relative to its total weight—
(A) from about 0.005 to about 5.0 wt. %, preferably from about 0.05 to about 3.0 wt. %, more preferably from about 0.1 to about 2.5 wt. %, even more preferably from about 0.3 to about 2.0 wt. % and most preferably from about 0.4 to about 0.9 wt. % 1-(2-hydroxyethyl)-4,5-diaminopyrazole sulfate.

The coupler 2,6-dihydroxy-3,4-dimethylpyridine (B) can—relative to the total weight of the agent—be used in quantity ranges from about 0.001 to about 3.5 wt. %. Color tints with particularly good gray coverage are achieved when 2,6-dihydroxy-3,4-dimethylpyridine (B) is used in a quantity range from about 0.1 to about 1.2 wt. %, preferably from about 0.2 to about 1.0 wt. % and more preferably from about 0.3 to about 0.7 wt. % 2,6-dihydroxy-3,4-dimethylpyridine (relative to the total weight of the agent).

In another particularly preferred embodiment, an agent as contemplated herein contains—relative to its total weight—
(B) from about 0.001 to about 3.5 wt. %, preferably from about 0.1 to about 1.2 wt. %, more preferably from about 0.2 to about 1.0 wt. % and even more preferably from about 0.3 to about 0.7 wt. % 2,6-dihydroxy-3,4-dimethylpyridine.

It has emerged that the addition of at least one developer from the group (C) to form the combination of (A) and (B) is essential to improving the gray coverage. To obtain a copper tint with high brilliance as well as optimizing the gray coverage, the developer(s) C should be used within specific quantity ranges.

The agents as contemplated herein can contain one or more compounds (C) from the group of p-phenylendiamine, toluene-2,5-diamine, 2-(2,5-diaminophenyl)ethanol and/or the physiologically-tolerated salts of said compounds in a total quantity from about 0.005 to about 5 wt. %. The use of one or more compounds from the group (C) in a total quantity from about 0.07 to about 0.70 wt. %, more preferably from about 0.07 to about 0.35 wt. % and most preferably from about 0.11 to about 0.30 wt. % has proved to be particularly advantageous.

In another particularly preferred embodiment, an agent as contemplated herein contains—relative to its total weight— (C) from about 0.005 to about 5.0 wt. %, preferably from about 0.07 to about 0.70 wt. %, more preferably from about 0.07 to about 0.35 wt. % and most preferably from about 0.11 to about 0.30 wt. % toluene-2,5-diamine sulfate.

Accordingly, an agent for the oxidative dyeing of keratinous fibers, containing in a cosmetic carrier—relative to the total weight of the agent—
(A) from about 0.005 to about 5.0 wt. % 1-(2-hydroxyethyl)-4,5-diaminopyrazole sulfate and
(B) from about 0.001 to about 3.5 wt. % 2,6-dihydroxy-3,4-dimethylpyridine and
(C) from about 0.005 to about 5.0 wt. % toluene-2,5-diamine sulfate, is particularly preferred.

An agent for the oxidative dyeing of keratinous fibers, containing in a cosmetic carrier—relative to the total weight of the agent—
(A) from about 0.05 to about 3.0 wt. % 1-(2-hydroxyethyl)-4,5-diaminopyrazole sulfate and
(B) from about 0.01 to about 1.2 wt. % 2,6-dihydroxy-3,4-dimethylpyridine and
(C) from about 0.07 to about 0.70 wt. % toluene-2,5-diamine sulfate is particularly preferred.

An agent for the oxidative dyeing of keratinous fibers, containing in a cosmetic carrier—relative to the total weight of the agent—
(A) from about 0.1 to about 2.5 wt. % 1-(2-hydroxyethyl)-4,5-diaminopyrazole sulfate
(B) from about 0.2 to about 1.0 wt. % 2,6-dihydroxy-3,4-dimethylpyridine and
(C) from about 0.07 to about 0.35 wt. % toluene-2,5-diamine sulfate is particularly preferred.

An agent for the oxidative dyeing of keratinous fibers, containing in a cosmetic carrier—relative to the total weight of the agent—
(A) from about 0.3 to about 2.0 wt. % 1-(2-hydroxyethyl)-4,5-diaminopyrazole sulfate
(B) from about 0.3 to about 0.7 wt. % 2,6-dihydroxy-3,4-dimethylpyridine and
(C) from about 0.11 to about 0.30 wt. % toluene-2,5-diamine sulfate is particularly preferred.

An agent for the oxidative dyeing of keratinous fibers, containing in a cosmetic carrier—relative to the total weight of the agent—
(A) from about 0.4 to about 0.9 wt. % 1-(2-hydroxyethyl)-4,5-diaminopyrazole sulfate
(B) from about 0.3 to about 0.7 wt. % 2,6-dihydroxy-3,4-dimethylpyridine and
(C) from about 0.11 to about 0.30 wt. % toluene-2,5-diamine sulfate is particularly preferred.

More particularly, attractive copper tints with very good gray coverage was also achieved by using, as the coupler from the group (C), 2-(2,5-diaminophenyl)ethanol sulfate in specific quantity ranges in the agents as contemplated herein.

In another particularly preferred embodiment, an agent as contemplated herein contains—relative to its total weight— (C) from about 0.007 to about 5.3 wt. %, preferably from about 0.09 to about 0.90 wt. %, more preferably from about 0.15 to about 0.55 wt. % and most preferably from about 0.20 to about 0.35 wt. % 2-(2,5-diaminophenyl)ethanol sulfate.

Therefore, an agent for the oxidative dyeing of keratinous fibers, containing in a cosmetic carrier—relative to the total weight of the agent—
(A) from about 0.005 to about 5.0 wt. % 1-(2-hydroxyethyl)-4,5-diaminopyrazole sulfate and
(B) from about 0.001 to about 3.5 wt. % 2,6-dihydroxy-3,4-dimethylpyridine and
(C) from about 0.007 to about 5.3 wt. % 2-(2,5-diaminophenyl)ethanol sulfate is also particularly preferred.

An agent for the oxidative dyeing of keratinous fibers, containing in a cosmetic carrier—relative to the total weight of the agent—
(A) from about 0.05 to about 3.0 wt. % 1-(2-hydroxyethyl)-4,5-diaminopyrazole sulfate and
(B) from about 0.01 to about 1.2 wt. % 2,6-dihydroxy-3,4-dimethylpyridine and
(C) from about 0.09 to about 0.90 wt. % 2-(2,5-diaminophenyl)ethanol sulfate is particularly preferred.

An agent for the oxidative dyeing of keratinous fibers, containing in a cosmetic carrier—relative to the total weight of the agent—
(A) from about 0.1 to about 2.5 wt. % 1-(2-hydroxyethyl)-4,5-diaminopyrazole sulfate
(B) from about 0.2 to about 1.0 wt. % 2,6-dihydroxy-3,4-dimethylpyridine and
(C) from about 0.15 to about 0.55 wt. % 2-(2,5-diaminophenyl)ethanol sulfate is particularly preferred.

An agent for the oxidative dyeing of keratinous fibers, containing in a cosmetic carrier—relative to the total weight of the agent—
(A) from about 0.3 to about 2.0 wt. % 1-(2-hydroxyethyl)-4,5-diaminopyrazole sulfate
(B) from about 0.3 to about 0.7 wt. % 2,6-dihydroxy-3,4-dimethylpyridine and
(C) from about 0.20 to about 0.35 wt. % 2-(2,5-diaminophenyl)ethanol sulfate is particularly preferred.

An agent for the oxidative dyeing of keratinous fibers, containing in a cosmetic carrier—relative to the total weight of the agent—
(A) from about 0.4 to about 0.9 wt. % 1-(2-hydroxyethyl)-4,5-diaminopyrazole sulfate
(B) from about 0.3 to about 0.7 wt. % 2,6-dihydroxy-3,4-dimethylpyridine and
(C) from about 0.20 to about 0.35 wt. % 2-(2,5-diaminophenyl)ethanol sulfate is particularly preferred.

During the work leading to this present disclosure, it unexpectedly emerged that the gray coverage was able to be further improved by adding a second coupler group (D). The couplers from this second coupler group (D) are one or more m-dihydroxybenzol derivatives from the group of resorcin, 4-chlorresorcin and/or 2-methylresorcin. The fact that the addition of one or more couplers (D) did not result in an unattractive color shift was also unexpected.

In another most preferred embodiment, an agent for stabilizing keratin fibers as contemplated herein
(D) resorcin, 4-chlorresorcin and/or 2-methylresorcin.

Resorcin is a compound of the formula (VI), 2-methylresorcin is a compound of the formula (VII), and 4-chlorresorcin is a compound of the formula (VIII).

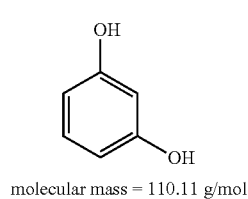

molecular mass = 110.11 g/mol   (VI)

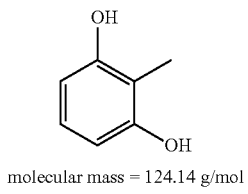

molecular mass = 124.14 g/mol   (VII)

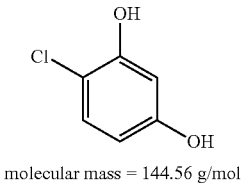

molecular mass = 144.56 g/mol   (VIII)

In this context, the best properties have been shown by resorcin and 2-methylresorcin as couplers from the group (D), more particularly when used in combination with toluene-2,5-diamine sulfate as the developer (C).

Accordingly, an agent for the oxidative dyeing of human hair, containing in a cosmetic carrier
(A) 1-(2-hydroxyethyl)-4,5-diaminopyrazole sulfate and
(B) 2,6-dihydroxy-3,4-dimethylpyridine and
(C) toluene-2,5-diamine sulfate and
(D) resorcin is also particularly preferred.

Therefore, an agent for the oxidative dyeing of human hair, containing in a cosmetic carrier
(A) 1-(2-hydroxyethyl)-4,5-diaminopyrazole sulfate and
(B) 2,6-dihydroxy-3,4-dimethylpyridine and
(C) toluene-2,5-diamine sulfate and
(D) 2-methylresorcin is also particularly preferred.

In order to achieve particularly bright tints with outstanding application-related properties, the coupler(s) from the group (D) are preferably used in specific quantity ranges. For example, the agents as contemplated herein can contain one or more couplers from the group (D) in a total quantity from about 0.001 to about 5 wt. %.

In another particularly preferred embodiment, an agent as contemplated herein contains—relative to its total weight—
(D) from about 0.001 to about 0.5 wt. %, preferably from about 0.01 to about 0.3 wt. %, more preferably from about 0.015 to about 0.25 wt. % resorcin.

In another particularly preferred embodiment, an agent as contemplated herein contains—relative to its total weight—
(D) from about 0.003 to about 0.55 wt. %, preferably from about 0.01 to about 0.35 wt. %, more preferably from about 0.020 to about 0.30 wt. % 2-methylresorcin.

Therefore, an agent for the oxidative dyeing of keratinous fibers, containing in a cosmetic carrier—relative to the total weight of the agent—
(A) from about 0.005 to about 5.0 wt. % 1-(2-hydroxyethyl)-4,5-diaminopyrazole sulfate and
(B) from about 0.001 to about 3.5 wt. % 2,6-dihydroxy-3,4-dimethylpyridine and
(C) from about 0.005 to about 5.0 wt. % toluene-2,5-diamine sulfate and.
(D) from about 0.001 to about 0.5 wt. % resorcin is explicitly most preferred.

An agent for the oxidative dyeing of keratinous fibers, containing in a cosmetic carrier—relative to the total weight of the agent—
(A) from about 0.05 to about 3.0 wt. % 1-(2-hydroxyethyl)-4,5-diaminopyrazole sulfate and
(B) from about 0.01 to about 1.2 wt. % 2,6-dihydroxy-3,4-dimethylpyridine and
(C) from about 0.07 to about 0.70 wt. % toluene-2,5-diamine sulfate and
(D) from about 0.01 to about 0.3 wt. % resorcin is explicitly most preferred.

An agent for the oxidative dyeing of keratinous fibers, containing in a cosmetic carrier—relative to the total weight of the agent—
(A) from about 0.1 to about 2.5 wt. % 1-(2-hydroxyethyl)-4,5-diaminopyrazole sulfate
(B) from about 0.2 to about 1.0 wt. % 2,6-dihydroxy-3,4-dimethylpyridine and
(C) from about 0.07 to about 0.35 wt. % toluene-2,5-diamine sulfate and
(D) from about 0.015 to about 0.25 wt. % resorcin is explicitly most preferred.

Therefore, an agent for the oxidative dyeing of keratinous fibers, containing in a cosmetic carrier—relative to the total weight of the agent—
(A) from about 0.005 to about 5.0 wt. % 1-(2-hydroxyethyl)-4,5-diaminopyrazole sulfate and
(B) from about 0.001 to about 3.5 wt. % 2,6-dihydroxy-3,4-dimethylpyridine and
(C) from about 0.11 to about 0.30 wt. % toluene-2,5-diamine sulfate and
(D) from about 0.003 to about 0.55 wt. % 2-methylresorcin is therefore also explicitly most preferred.

An agent for the oxidative dyeing of keratinous fibers, containing in a cosmetic carrier—relative to the total weight of the agent—
(A) from about 0.05 to about 3.0 wt. % 1-(2-hydroxyethyl)-4,5-diaminopyrazole sulfate and
(B) from about 0.01 to about 1.2 wt. % 2,6-dihydroxy-3,4-dimethylpyridine and
(C) from about 0.11 to about 0.30 wt. % toluene-2,5-diamine sulfate and
(D) from about 0.01 to about 0.35 wt. % 2-methylresorcin is explicitly most preferred.

An agent for the oxidative dyeing of keratinous fibers, containing in a cosmetic carrier—relative to the total weight of the agent—
(A) from about 0.1 to about 2.5 wt. % 1-(2-hydroxyethyl)-4,5-diaminopyrazole sulfate
(B) from about 0.2 to about 1.0 wt. % 2,6-dihydroxy-3,4-dimethylpyridine and
(C) from about 0.15 to about 0.55 wt. % toluene-2,5-diamine sulfate and
(D) from about 0.020 to about 0.30 wt. % 2-methylresorcin is explicitly most preferred.

Therefore, an agent for the oxidative dyeing of keratinous fibers, containing in a cosmetic carrier—relative to the total weight of the agent—

(A) from about 0.005 to about 5.0 wt. % 1-(2-hydroxyethyl)-4,5-diaminopyrazole sulfate and
(B) from about 0.001 to about 3.5 wt. % 2,6-dihydroxy-3,4-dimethylpyridine and
(C) from about 0.007 to about 5.3 wt. % 2-(2,5-diaminophenyl)ethanol sulfate and
(D) from about 0.001 to about 0.5 wt. % resorcin is explicitly most preferred.

An agent for the oxidative dyeing of keratinous fibers, containing in a cosmetic carrier—relative to the total weight of the agent—
(A) from about 0.05 to about 3.0 wt. % 1-(2-hydroxyethyl)-4,5-diaminopyrazole sulfate and
(B) from about 0.01 to about 1.2 wt. % 2,6-dihydroxy-3,4-dimethylpyridine and
(C) from about 0.09 to about 0.90 wt. % 2-(2,5-diaminophenyl)ethanol sulfate and
(D) from about 0.01 to about 0.3 wt. % resorcin is explicitly most preferred.

An agent for the oxidative dyeing of keratinous fibers, containing in a cosmetic carrier—relative to the total weight of the agent—
(A) from about 0.1 to about 2.5 wt. % 1-(2-hydroxyethyl)-4,5-diaminopyrazole sulfate
(B) from about 0.2 to about 1.0 wt. % 2,6-dihydroxy-3,4-dimethylpyridine and
(C) from about 0.15 to about 0.55 wt. % 2-(2,5-diaminophenyl)ethanol sulfate and
(D) from about 0.015 to about 0.25 wt. % resorcin is explicitly most preferred.

Therefore, an agent for the oxidative dyeing of keratinous fibers, containing in a cosmetic carrier—relative to the total weight of the agent—
(A) from about 0.005 to about 5.0 wt. % 1-(2-hydroxyethyl)-4,5-diaminopyrazole sulfate and
(B) from about 0.001 to about 3.5 wt. % 2,6-dihydroxy-3,4-dimethylpyridine and
(C) from about 0.007 to about 5.3 wt. % 2-(2,5-diaminophenyl)ethanol sulfate and
(D) from about 0.003 to about 0.55 wt. % 2-methylresorcin is therefore also explicitly most preferred.

An agent for the oxidative dyeing of keratinous fibers, containing in a cosmetic carrier—relative to the total weight of the agent—
(A) from about 0.05 to about 3.0 wt. % 1-(2-hydroxyethyl)-4,5-diaminopyrazole sulfate and
(B) from about 0.01 to about 1.2 wt. % 2,6-dihydroxy-3,4-dimethylpyridine and
(C) from about 0.09 to about 0.90 wt. % 2-(2,5-diaminophenyl)ethanol sulfate and
(D) from about 0.01 to about 0.35 wt. % 2-methylresorcin is explicitly most preferred.

An agent for the oxidative dyeing of keratinous fibers, containing in a cosmetic carrier—relative to the total weight of the agent—
(A) from about 0.1 to about 2.5 wt. % 1-(2-hydroxyethyl)-4,5-diaminopyrazole sulfate
(B) from about 0.2 to about 1.0 wt. % 2,6-dihydroxy-3,4-dimethylpyridine and
(C) from about 0.15 to about 0.55 wt. % 2-(2,5-diaminophenyl)ethanol sulfate and
(D) from about 0.020 to about 0.30 wt. % 2-methylresorcin is explicitly most preferred.

As already described above, tints with outstanding gray coverage were achieved by using oxidation dye precursors from the groups (A), (B) and (C) in specific quantity ratios.

For this reason, the agents of another particularly preferred embodiment are exemplified in that the weight ratio of (A) to (B), i.e. the weight ratio (A)/(B), is from about 0.7 to about 2.0, preferably from about 0.9 to about 1.9, more preferably from about 1.1 to about 1.8 and most preferably from about 1.3 to about 1.6.

The weight ratio (A)/(B) is the weight ratio of all developers from the group (A) contained in the agent to the coupler (B) 2,6-dihydroxy-3,4-dimethylpyridine.

Example: A dye cream contains in a cosmetic carrier, in addition to other optional constituents
(A) about 0.70 wt. % 1-(2-hydroxyethyl)-4,5-diaminopyrazole sulfate
(B) about 0.45 wt. % 2,6-dihydroxy-3,4-dimethylpyridine and
(C) about 0.13 wt. % toluene-2,5-diamine sulfate.

The weight ratio (A)/(B) is (0.70 wt. %/0.45 wt. %)=1.56.

Moreover, the agents of a most preferred embodiment are also exemplified in that the weight ratio of (A) to (C), i.e. the weight ratio (A)/(C), is from about 1.0 to about 8.0, preferably from about 2.0 to about 7.0, even more preferably from about 3.0 to about 6.0 and most preferably from about 4.5 to about 5.5.

The weight ratio (A)/(C) is the weight ratio of all developers from group (A) contained in the agent to all developers from group (C) contained in the agent.

Example: A dye cream as contemplated herein contains in the cosmetic carrier
(A) about 0.70 wt. % 1-(2-hydroxyethyl)-4,5-diaminopyrazole sulfate
(B) about 0.45 wt. % 2,6-dihydroxy-3,4-dimethylpyridine and
(C) about 0.13 wt. % toluene-2,5-diamine sulfate.

The weight ratio (A)/(C) is (0.70 wt. %/0.13 wt. %)=5.38.

If the oxidation dye precursors from the four groups of (A), (B), (C) and (D) were used in specific quantity ratios to one another, both the fastness properties as well as, in particular, the gray coverage, was able to be further improved.

Moreover, the agents of a most preferred embodiment are also exemplified in that the weight ratio of (A) to (D), i.e. the weight ratio (A)/(D), is from about 5.0 to about 60.0, preferably from about 10.0 to about 55.0, even more preferably from about 15.0 to about 50.0 and most preferably from about 20.0 to about 45.0.

The weight ratio (A)/(D) is the weight ratio of all developers from group (A) contained in the agent to all couplers from group (G) contained in the agent.

In other words, particularly good coverage in particular was able to be observed when only a relatively small quantity of coupler (D) was added to the agent as contemplated herein, and therefore the total quantity of developers (A) in the agent was from about 20 to about 45-times more than the quantity of couplers (D).

Example: A dye cream as contemplated herein contains in the cosmetic carrier
(A) about 0.70 wt. % 1-(2-hydroxyethyl)-4,5-diaminopyrazole sulfate
(B) about 0.43 wt. % 2,6-dihydroxy-3,4-dimethylpyridine and
(C) about 0.13 wt. % toluene-2,5-diamine sulfate and
(D) about 0.03 wt. % resorcin The weight ratio (A)/(D) is (0.70 wt. %/0.03 wt. %)=23.33.

For further tinting, the agents as contemplated herein can also contain other oxidation dye precursors of the developer type and/or of the coupler type, which are different to the developers and couplers from the groups (A), (B), (C) and (D).

Preferred additional oxidation dye precursors of the developer type can be selected from the group formed from 2-(1,2-dihydroxyethyl)-p-phenylendiamine, N,N-bis-(2-hydroxyethyl)-p-phenylendiamine, 2-methoxymethyl-p-phenylendiamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diamino-propane-2-ol, bis-(2-hydroxy-5-aminophenyl)methane, 1,3-bis-(2,5-di aminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one and the physiologically-tolerated salts thereof.

In a particularly preferred embodiment, the agent as contemplated herein, however, contains no other oxidation dye precursors of the developer type.

An agent for the oxidative dyeing of keratinous fibers, containing in a cosmetic carrier
(A) 1-(2-Hydroxyethyl)-4,5-diaminopyrazole and/or one of the physiologically-tolerated salts thereof and
(B) 2,6-dihydroxy-3,4-dimethylpyridine and
(C) p-phenylendiamine, toluene-2,5-diamine, 2-(2,5-diaminophenyl)ethanol and of one of the physiologically-tolerated salts thereof is al so preferred,
providing that it contains no developers other than those from the groups (A) and (C).

An agent for the oxidative dyeing of keratinous fibers, containing in a cosmetic carrier
(A) 1-(2-Hydroxyethyl)-4,5-diaminopyrazole and/or one of the physiologically-tolerated salts thereof and
(B) 2,6-dihydroxy-3,4-dimethylpyridine and
(C) p-phenylendiamine, toluene-2,5-diamine, 2-(2,5-diaminophenyl)ethanol and of one of the physiologically-tolerated salts thereof is al so preferred,
providing that the agent contains no compound from the group of N,N-bis-(2-hydroxyethyl)-p-phenylendiamine, 4-amino-3-methylphenol, 2-methoxymethyl-p-phenylendiamine, p-aminophenol, 4-amino-2-aminomethylphenol, 2,4,5,6-tetraaminopyrimidine, 4-hydroxy-2,5,6-triaminopyrimidine and 2-hydroxy-4,5,6-triaminopyrimidine.

Coupler components that can be contained in addition are preferably selected from the following classes: m-aminophenol, o-aminophenol, m-diaminobenzol, o-diaminobenzol and/or the derivatives thereof; naphthalene derivatives having at least one hydroxy group; trihydroxybenzol derivatives; pyridine derivatives; pyrimidine derivatives; indole derivatives and indoline derivatives; pyrazolone derivatives (for example, 1-phenyl-3-methylpyrazol-5-one); morpholine derivatives (for example, 6-hydroxybenzomorpholines or 6-aminobenzomorpholines); chinoxaline derivatives (for example, 6-methyl-1,2,3,4-tetrahydrochinoxaline), as well as mixtures from two or more compounds from one or more of said classes.

Preferred additional m-aminophenol coupler components are selected from at least one compound from the group of 3-aminophenol, 5-amino-2-methylphenol, N-cyclopentyl-3-aminophenol, 3-amino-2-chlor-6-methylphenol, 2-hydroxy-4-aminophenoxyethanol, 2,6-dimethyl-3-aminophenol, 3-tri fluoroacetyl amino-2-chlor-6-methyl phenol, 5-amino-4-chlor-2-methylphenol, 5-amino-4-methoxy-2-methylphenol, 5-(2'-hydroxyethyl)amino-2-methylphenol, 3-diethylaminophenol, N-cyclopentyl-3-aminophenol, 1,3-dihydroxy-5-(methylamino)benzol, 3-ethylamino-4-methylphenol, 2,4-dichlor-3-aminophenol and the physiologically-tolerated salts thereof. Preferred m-diaminobenzol coupler components are selected from at least one compound from the group of m-phenylendiamine, 2-(2,4-diaminophenoxy)ethanol, 1,3-bis(2,4-diaminophenoxy)propane, 1-methoxy-2-amino-4-(2'-hydroxyethylamino)benzol, 1,3-bis(2,4-diaminophenyl)propane, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-to-(2'-hydroxyethyl)aminobenzol and the physiologically-tolerated salts thereof. Preferred o-diaminobenzol coupler components are selected from at least one compound from the group of 3,4-diaminobenzoic acid and 2,3-diamino-1-methylbenzol and the physiologically-tolerated salts thereof. Preferred naphthaline derivatives having at least one hydroxy group are selected from at least one compound from the group of 1-naphthol, 2-methyl-1-naphthol, 2-hydroxymethyl-1-naphthol, 2-hydroxyethyl-1-naphthol, 1,3-dihydroxynaphthaline, 1,5-dihydroxynaphthaline, 1,6-dihydroxynaphthaline, 1,7-dihydroxynaphthaline, 1,8-dihydroxynaphthaline, 2,7-dihydroxynaphthaline and 2,3-dihydroxynaphthaline. Preferred trihydroxybenzols and the derivatives thereof are selected from at least one compound from the group of pyrogallol and 1,2,4-trihydroxybenzol. Preferred pyridine derivatives are selected from at least one compound from the group of 2,6-dihydroxypyridine, 2-amino-3-hydroxypyridine, 2-amino-5-chlor-3-hydroxypyridine, 3-amino-2-methylamino-6-methoxypyridine, 2,6-dihydroxy-4-methylpyridine, 2,6-diaminopyridine, 2,3-diamino-6-methoxypyridine, 3,5-diamino-2,6-dimethoxypyridine, 3,4-diaminopyridine, 2-(2-methoxyethyl)amino-3-amino-6-methoxypyridine, 2-(4'-methoxyphenyl)amino-3-aminopyridine, and the physiologically-tolerated salts thereof. Preferred pyrimidine derivatives are selected from at least one compound from the group of 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine and 4,6-dihydroxy-2-methylpyrimidine and the physiologically-tolerated salts thereof. Preferred indole derivatives are selected from at least one compound of the group 4-hydroxyindole, 6-hydroxyindole and 7-hydroxyindole and the physiologically-tolerated salts thereof. Preferred indoline derivatives are selected from at least one compound of the group 4-hydroxyindoline, 6-hydroxyindoline and 7-hydroxyindoline and the physiologically-tolerated salts thereof.

Particularly preferred additional coupler components as contemplated herein are selected from 3-aminophenol, 5-amino-2-methylphenol, 3-amino-2-chlor-6-methylphenol, 2-hydroxy-4-aminophenoxy ethanol, 5-amino-4-chlor-2-methylphenol, 5-(2-hydroxyethyl)-amino-2-methylphenol, 2,4-dichlor-3-aminophenol, 2-aminophenol, 3-phenylendiamine, 2-(2,4-diaminophenoxy)ethanol, 1,3-bis(2,4-diaminophenoxy)propane, 1-methoxy-2-amino-4-(2-hydroxyethylamino)benzol, 1,3-bis(2,4-diaminophenyl)propane, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino) ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzol, 2,4-trihydroxybenzol, 2-amino-3-hydroxypyridine, 3-amino-2-methylamino-6-methoxypyridine, 3,5-diamino-2,6-dimethoxypyridine, 1-phenyl-3-methylpyrazol-5-one, 1-naphthole, 1,5-dihydroxynaphthaline, 2,7-dihydroxynaphthaline, 1,7-dihydroxynaphthaline, 1,8-dihydroxynaphthaline, 4-hydroxyindole, 6-hydroxyindole, 7-hydroxyindole, 4-hydroxyindoline, 6-hydroxyindoline, 7-hydroxyindoline or mixtures of said compounds or the physiologically-tolerated salts thereof. Resorcin, 2-methylresorcin, 5-amino-2-methylphenol, 3-aminophenol, 2-(2,4-diaminophenoxy)ethanol, 1,3-bis(2,4-diaminophenoxy)propane, 1-methoxy-2-amino-4-(2'-hydroxyethylamino)benzol, 2-amino-3-hydroxypyridine and 1-naphthol, as well as the physiologically-tolerated salts thereof are most preferred.

The use of 2-amino-3-hydroxypyridine as a further coupler (E) is most preferred. In another most preferred embodiment, an agent as contemplated herein contains (E) 2-amino-3-hydroxypyridine.

Essentially, the agents as contemplated herein can contain at least one partially-oxidizing dye from the group of the anionic, non-ionic and/or cationic dyes.

One or more non-ionic, partially-oxidizing dyes from the group of HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, 1,4-diamino-2-nitrobenzol, 2-amino-4-nitrophenol, 1,4-bis-(2-hydroxyethyl)-amino-2-nitrobenzol, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzol, 1-amino-4-(2-hydroxyethyl)amino-5-chlor-2-nitrobenzol, 4-amino-3-nitrophenol, 1-(2'-Ureidoethyl)amino-4-nitrobenzol, 2-[(4-amino-2-nitrophenyl)amino]benzoic acid, 4-[(3-hydroxypropyl)amino]-3-nitrophenol, 4-nitro-o-phenylendiamine, 6-nitro-1,2,3,4-tetrahydrochinoxaline, 2-hydroxy-1,4-naphthoquinone, picramic acid and the salts thereof, 2-amino-6-chloro-4-nitrophenol, 4-ethylamino-3-nitrobenzoic acid and 2-chlor-6-ethylamino-4-nitrophenol are particularly preferred.

In another particularly preferred embodiment, an agent as contemplated herein additionally contains one or more non-ionic direct dyes from the group of HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, HC Blue 15, Disperse Blue 3, HC Violet 1, Disperse Violet 1, Disperse Violet 4, Disperse Black 9, 1,4-diamino-2-nitrobenzol, 2-amino-4-nitrophenol, 1,4-bis(2-hydroxyethyl)-amino-2-nitrobenzol, 3-nitro-4-(2-hydroxyethyl)aminophenol, 2-(2-hydroxyethyl)amino-4,6-dinitrophenol, 4-[(2-hydroxyethyl)amino]-3-nitro-1-methyl benzol, 1-amino-4-(2-hydroxyethyl)amino-5-chloro-2-nitrobenzol, 4-amino-3-nitrophenol, 1-(2'-ureidoethyl)amino-4-nitrobenzol, 2-[(4-amino-2-nitrophenol)amino]benzoic acid, 4-[(3-hydroxypropyl)amino]-3-nitrophenol, 4-nitro-o-phenylenediamine, 6-nitro-1,2,3,4-tetrahydrochinoxaline, 2-hydroxy-1,4-naphthoquinone, picramic acid and the salts thereof, 2-amino-6-chloro-4-nitrophenol, 4-(ethylamino)-3-nitrobenzoic acid and 2-chlor-6-ethylamino-4-nitrophenol.

Anionic partially-oxidizing dyes, which are known under the international designations or trade names of Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, bromophenol blue and tetrabromophenol blue, can be contained in addition.

Suitable cationic partially-oxidizing dyes are cationic triphenylmethane dyes, such as Basic Blue 7, Basic Blue 26, Basic Violet 2 and Basic Violet 14, aromatic systems, which are substituted with a quaternary nitrogen group, such as Basic Yellow 57, Basic Red 76, Basic Blue 99, Basic Brown 16 and Basic Brown 17, cationic anthraquinone dyes, such as HC Blue 16 (Bluequat B), as well as partially-oxidizing dyes containing a heterocyclus, which has at least one quaternary nitrogen atom, more particularly Basic Yellow 87, Basic Orange 31 and Basic Red 51. The cationic partially-oxidizing dyes, which are sold under the trade name of Arianor, are also suitable cationic partially-oxidizing dyes as contemplated herein.

The additional oxidation dye precursors, i.e. developer components and coupler components, which differ from the compounds of groups (A), (B), (C) and (D), as well as the optionally additionally contained partially-oxidizing dyes can, for example, be used in a total quantity of from about 0.0001 to about 5.0 wt. %, preferably from about 0.001 to about 3.5 wt. %, relative to the total weight of the agent as contemplated herein in each case.

The agent as contemplated herein described above is the agent containing the oxidation dye precursor, i.e. a dye cream. To produce the ready-to-use oxidative dye and to initiate the dye formation reaction, this dye cream (referred to below as component K1) is mixed with a second component K2, which contains an oxidant.

To avoid incompatibilities and to prevent premature, unwanted dye formation, the components K1 (dye cream) and K2 (oxidant preparation) are always packaged separately from one another and brought into contact with one another only shortly before application.

A second subject matter of the present disclosure is therefore a method for the oxidative dyeing of keratinous fibers, comprising the following steps in the stated sequence
(i) Production of a ready-to-use agent for lightening keratinous fibers by mixing a first component (K1) with a second component (K2),
(ii) Distribution of the ready-to-use agent onto the keratinous fibers,
(iii) Leaving the agent on the fibers for a period from about 1 to about 60 minutes and
(iv) Washing the agent out of the fibers,
wherein
the first component (K1) is an agent of the first subject matter of the present disclosure and
the second component (K2) is an oxidant preparation, which contains hydrogen peroxide.

The first component is the—preferably set to alkali pH—dye preparation (K1), which contains the oxidant dye precursors (A), (B), (C) and where applicable (D), (as well as, where applicable, other additional oxidation dye precursors and/or other partially oxidizing dyes).

Before application, this dye preparation is mixed with an oxidation dye precursor (K2). For reasons of stability, the oxidant preparation (K2) is preferably set to an acid pH value and contains the oxidant. The oxidant is hydrogen peroxide, which is mostly used in the form of its hydrous solution.

The components (K1) and (K2) can be mixed with one another in various weight ratios (K1)/(K2) from, for example, about 0.3 to about 3.0, preferably from about 0.5 to about 2.5, and most preferably from about 0.45 to about 1.5.

A particularly preferred method is exemplified in that the first component (K1) and the second component (K2) are mixed with one another in a weight ratio of (K1)/(K2) from about 0.3 to about 3.0, preferably from about 0.5 to about 2.5, and most preferably from about 0.45 to about 1.5.

All oxidation dye precursors are contained in the dye preparation (K1). Therefore, all weight quantity values and weight ratios of the oxidation dye precursors disclosed in the description refer to the total weight of the dye preparation (K1).

Shortly before application, the agent as contemplated herein (corresponding to the dye preparation (K1)) is mixed with an oxidant preparation (i.e. with the oxidant component (K2)). This ready-to-use oxidative dye is prepared in this way.

To ensure adequate moisture expansion of the keratin fibers, the ready-to-use oxidative dye is preferably set to an alkali pH value. The dye processes on keratin fibers usually occur in an alkali environment. To protect the keratin fibers and also the skin to the greatest possible degree, setting too high a pH value is however not desirable. Therefore, the ready-to-use agent preferably has a pH value from about 8.0 to about 10.5, more preferably from about 8.7 to about 10.3, even more preferably from about 9.0 to about 10.2 and most preferably from about 9.2 to about 10.1. The pH values are values that were measured at a temperature of about 22° C. with a glass electrode.

The alkalizing agents required to set the alkali pH value are usually packaged together with the oxidation dye precursors in the component K1. The alkalizing agents usable as contemplated herein can be selected from the group formed from ammonia, alkanolamines, basic amino acids, as well as inorganic alkalizing agents, such as (earth) alkali metal hydroxides, (earth) alkali metal metasilicates, (earth) alkali metal phosphates and (earth) alkali metal hydrogen phosphates. Preferred inorganic alkalizing agents are sodium hydroxide, sodium hydroxide, sodium silicate and sodium metasilicate. Organic alkalizing agents usable as contemplated herein are preferably selected from monoethanolamine, 2-amino-2-methylpropanol and triethanolamine. The basic amino acids usable as alkalizing agents as contemplated herein are preferably selected from the group formed from arginine, lysine, ornithine, and histidine, most particularly arginine. However, it emerged during the examinations of the present disclosure that other agents preferred as contemplated herein are exemplified in that they additionally contain an organic alkalizing agent. One embodiment of the first subject matter of the present disclosure is exemplified in that the agent additionally contains at least one alkalizing agent, which is selected from the group formed from ammonia, alkanolamines and basic amino acids, more particularly from ammonia, monoethanolamine and arginine or the tolerated salts thereof. The alkalizing agent(s) is or are preferably packaged in the dye preparation (K1) together with the oxidation dye precursors.

The second component (K2) is an oxidant preparation containing hydrogen peroxide. In a preferred embodiment, hydrogen peroxide itself, as a hydrous solution, is used in the oxidant preparation (K2). The concentration of a hydrogen peroxide solution in the dye preparation (K2) is determined on the one hand by legal requirements and, on the other hand, by the desired effect; the use of from about 6 to about 12 wt. % solutions in water is preferred. Preparations preferred as contemplated herein (K2) are exemplified in that they contain from about 5 to about 20 wt. %, preferably from about 1 to about 12.5 wt. %, more preferably from about 2.5 to about 10 wt. % and most preferably from about 3 to about 6 wt. % of hydrogen peroxide, relative to the total weight of the agent in each case.

To increase the lightening effect, the dye preparation (K1) and/or the oxidant preparation (K2) can contain further bleach power enhancers, such as tetraacetylethylendiamine (TAED), 1,5-di acetyl-2,4-di oxohexahydro-1,3,5-triazine (DADHT), tetraacetylglykoluril (TAGU), N-nonanoylsuccinimide (NOSI), n-nonanoyl- or isononanoyloxybenzolsulfonate (n- and/or i-NOBS), phthalic anhydride, triacetine, ethylenglykoldiacetate and 2,5-diacetoxy-2,5-dihydrofurane, as well as carbonte salts and/or hydrogen carbonate salts, more particularly ammonium hydrogen carbonate, ammonium carbonate, sodium hydrogen carbonate, di-sodium carbonate, potassium hydrogen carbonate, di-potassium carbonate and calcium carbonate, and nitrogen-containing, heterocyclic bleach power enhancers, such as 4-acetyl-1-methylpyridinium-p-toluolsulfonate, 2-acetyl-1-methylpyridinium-p-toluolsulfonate, as well as N-methyl-3,4-dihydroisochinolinium-p-toluolsulfonate.

To further increase the lightening effect, the dye preparation (K1) and/or the oxidant preparation (K2) can additionally contain at least one $SiO_2$ compound, such as silica or silicate, more particularly soluble glasses. The SiO2 compound can be contained in the dye preparation (K1) and/or in the oxidant preparation (K2). As contemplated herein, it can be preferable to use the $SiO_2$ compounds in quantities from about 0.05 wt. % to about 15 wt. %, more preferable in quantities from about 0.15 wt. % to about 10 wt. % and most preferable in quantities from about 0.2 wt. % to about 5 wt. %, in each case, relative to the total weight of the dye preparation (K1) and/or the total weight of the oxidant preparation (K2). Each of the quantity values refers to the content of the $SiO_2$ compounds (excluding the water content thereof).

The oxidative colorant (i.e. the dye preparation (K1) and/or the oxidant preparation (K2)) can also contain additional active ingredients, excipients and admixtures, in order to improve the color and/or lightening effect and achieve further desired properties of the agent.

The ready-to-use dyes are preferably provided as liquid preparations and, therefore, another surfactant can also be added to the agents, wherein such surfactants are referred to as tensides or emulsifiers, depending on the field of application: These are preferably selected from anionic, zwitterionic, amphoteric and non-ionic tensides and emulsifiers.

In another embodiment, the dye preparation (K1) and/or the oxidant preparation (K2) can also be exemplified in that they contain at least one anionic tenside. Preferred anionic tensides are fatty acids, alkyl sulfates, alkyl ether sulfates and ether carboxylic acids having 10 to 20 C-atoms per alkyl group and up to 16 glycol ether groups per molecule.

Moreover, the dye preparation (K1) and/or the oxidant preparation (K2) can also be exemplified in that they contain at least one zwitterionic tenside. Preferred zwitterionic tensides are betaines, N-alkyl-N,N-dimethylammonium-glycinates, N-acyl-aminopropyl-N,N-dimethylammoniumglycinates, and 2-alkyl-3-carboxymethyl-3-hydroxyethyl-imidazolines. A preferred zwitterionic tenside is known under the INCI trade name of Cocamidopropyl Betaine.

Moreover, the dye preparation (K1) and/or the oxidant preparation (K2) can also be exemplified in that they contain at least one amphoteric tenside. Preferred amphoteric tensides are N-alkylglycines, N-alkylpropionic acids, N-alkylamino butyric acids, N-alkyliminodipropionic acids, N-hydroxyethyl-N-alkylamidopropylglycines, N-alkyltaurines, N-alkylsarcosines, 2-alkylaminopropionic acids and alkylamino acetic acids. Particularly preferred amphoteric tensides are N-cocosalkylaminopropionate, cocosacylamino-ethylaminopropionate and C12-C18 acylsarcosin.

It has also proven advantageous for the dye preparation (K1) and/or the oxidant preparation (K2) to contain other, non-ionogenic surfactants. Preferred non-ionic tensides are alkyl polyglycosides, as well as alkylene oxide binding agents to fatty alcohols and fatty acids having from about 2 to about 30 mol ethylene oxide per mol of fatty alcohol or fatty acid. Preparations with outstanding properties are also obtained if they contain fatty acid esters of ethoxylated glycerol as nonionic tensides.

The non-ionic, zwitterionic or amphoteric tensides are used in proportions from about 0.1 to about 45 wt. %, preferably from about 1 to about 30 wt. % and more preferably from about 1 to about 15 wt. %, relative on the total quantity of the ready-to-use agent.

The dye preparation (K1) and/or the oxidant preparation (K2) can also contain at least one thickening agent. Essentially, there are no restrictions with respect to said thickening agent. Both organic and purely inorganic thickening agents can be used.

Suitable thickening agents are anionic, synthetic polymers, cationic, synthetic polymers, naturally-occurring thickening agents, such as non-ionic guargums, scleroglucangums or xanthangums, rubber arabicum, Ghatti rubber, Karaya rubber, Tragant rubber, Carrageen rubber, Agar-Agar, locust bean gum, pectines, alginates, starch fractions and derivatives, such as amylose, amylopectin and dextrines, as well as cellulose derivatives, such as methyl cellulose, carboxyalkyl celluloses and hydroxyalkyl celluloses, non-ionic, fully-synthetic polymers, such as polyvinyl alcohol or polyvinyl pyrrolidinon; as well as inorganic thickening agents, more particularly layer silicates such as Bentonit, even more particularly Smektite, as well as Montmorillonit or Hectorit.

It has also proven advantageous for the dyes to contain at least one stabilizer or complexing agent, particularly if they additionally contain hydrogen peroxide. Particularly preferred stabilizers are phenacetin, alkali benzoates (sodium benzoate) and salicylic acid. Moreover, all complexing agents of the prior art can be used. Complexing agents preferred as contemplated herein are nitrogen-containing polycarboxylic acids, more particularly EDTA and EDDS, and phosphonates, more particularly 1-hydroxyethane-1,1-diphosphonate (HEDP) and/or ethylendiamintetramethylenphosphonate (ED TMP) and/or diethylentriaminpentamethylenphosphonate (DTPMP) and/or the sodium salts thereof.

The agents as contemplated herein (i.e. the dye preparation (K1) and/or the oxidant preparation (K2) can also contain other active ingredients, excipients and admixtures, such as non-ionic polymers, such as vinylpyrrolidinon/vinylacrylat-copolymers, polyvinylpyrrolidinon, vinylpyrrolidinon/vinylacetat-copolymers, polyethylenglycols and polysiloxanes; additional silicones such as volatile or non-volatile, straight-chained, branched or cyclical, cross-linked or non-cross-linked polyalkylsiloxanes (such as dimethicones or cyclomethicones), polyarylsiloxanes and/or polyalkylarylsiloxanes, more particularly polysiloxanes with organofunctional groups such as substituted or unsubstituted amines (amodimethicones), carboxyl-, alkoxy- and/or hydroxyl groups (dimethiconcopolyols), lineare polysiloxan (A)-polyoxyalkylen(B)-block copolymers, grafted silicon polymers; cationic polymers such as quaternized cellulose ether, polysiloxanes with quaternary groups, dimethyldiallylammoniumchlorid-polymers, acrylamid-dimethyldiallyl-ammonium chloride copolymers, with diethyl sulfate quaternated dimethylamino-ethylmethacrylat-vinylpyrrolidinon-copolymers, vinylpyrrolidinon-imidazolinium-methochlorid-copolymers and quaternated polyvinyl alcohol; zwitterionic and amphoteric polymers; anionic polymers such as polyacryl acids or cross-linked polyacryl acids; structurants, such as glucose, malic acid and lactic acid, hair-conditioning compounds such as phospholipides, for example lecithin and cephalines; perfume oils, dimethylisosorbid and cyclodextrine; fiber structure-improving agents, more particularly mono-, di- and oligosaccharides, such as glucose, galactose, fructose, fruit sugar and lactose; dyes for coloring the preparations; anti-dandruff active ingredients such as piroctone olamine, zinc omadine and climbazol; amino acids and oligopeptides; protein hydrolysates on an animal and/or plant basis, as well as in the form of their fatty acid condensation products or, where applicable, anionically or cationically modified derivatives; plant oils; light stabilizers and UV blockers; active ingredients such as panthenol, pantothenic acid, pantolacton, allantoin, pyrrolidinoncarbonic acids and the salts thereof, as well as bisabolol; polyphenols, more particularlyhydroxy cinnamic acids, 6,7-dihydroxycumarines, hydroxybenzoic acids, catechins, tannins, flavanons, anthocyanidines, flavanons, flavons and flavonols; ceramides or pseudoceramides; vitamins, provitamins and vitamin precursors; plant extracts; fats and waxes such as fatty alcohols, beeswax, montan wax and paraffins; source and penetration substances such as glycerin, propylenglycolmonoethylether, carbonate, hydrogen carbonate, guanidine, urea, as well as primary, secondary and tertiary phosphates; opacifiers such as latex, styrene/PVP and styrene/acrylamide copolymers; pearl shine concentrates such as ethylenglycolmono- and -distearate as well as PEG-3-distearate; pigments as well as propellants such as propane-butane-mixtures, $N_2O$, dimethylether, $CO_2$ and air.

A person skilled in the art will choose said further substances depending on the desired properties of the agent. With respect to other optional components and the used quantities of said components, express reference is made to the relevant manuals known to a person skilled in the art. In the agents as contemplated herein, each of the active ingredients, excipients are preferably used in quantities from about 0.0001 to about 25 wt. %, particularly from about 0.0005 to about 15 wt. %, relative to the total weight of agent (A) and/or the oxidant preparation (K2).

With respect to other preferred embodiments of the method as contemplated herein, the statements made regarding the agents as contemplated herein apply mutatis mutandis.

EXAMPLES 1.1. Production of the Dye

The following dye creams have been produced (unless otherwise stated, all values refer to percentage by weight):

|  | Dye creams | | |
| --- | --- | --- | --- |
|  | V1 (comparison) | E1 (invention) | E2 (invention) |
| Cetearyl alcohol (C16/C18 fatty alcohols) | 6.6 | 6.6 | 6.6 |
| C12-C18 fatty alcohols | 2.4 | 2.4 | 2.4 |
| Ceteareth-20 | 0.6 | 0.6 | 0.6 |
| Ceteareth-12 | 0.6 | 0.6 | 0.6 |
| Lamesoft PO 65 (65% solution of Cocoglucoside and Glyceryloleat in water) | 2.0 | 2.0 | 2.0 |

-continued

| | Dye creams | | |
|---|---|---|---|
| | V1 (comparison) | E1 (invention) | E2 (invention) |
| Sodium laureth-6-carboxylate (21% solution in water) | 10.0 | 10.0 | 10.0 |
| Sodium laureth sulfate (3 EO), 26-28% solution in water | 2.8 | 2.8 | 2.8 |
| Copolymers from sodium acrylate and trimethyl ammoniopropylacrylamide chloride, 19-21% solution in water | 3.75 | 3.75 | 3.75 |
| Etidronic acid, 60% solution in water | 0.2 | 0.2 | 0.2 |
| Sodium sulfate | 0.4 | 0.4 | 0.4 |
| Ammonium sulfate | 0.5 | 0.5 | 0.5 |
| Ascorbic acid | 0.1 | 0.1 | 0.1 |
| Sodium hydroxide 50% hydrous solution | 0.5 | 0.5 | 0.5 |
| Sodium silicate 40/42 (sodium soluble glass) | 0.5 | 0.5 | 0.5 |
| L-Serin | 1.0 | 1.0 | 1.0 |
| Ammonia, 25% hydrous solution | 6.5 | 6.5 | 6.5 |
| 4.5-diamino-1-(2-hydroxyethyl)-1H-pyrazol sulfate | 0.841 | 0.697 | 0.697 |
| 2,6-dihydroxy-3,4-dimethylpyridine | 0.455 | 0.455 | 0.429 |
| p-toluylendiamine, sulfate | — | 0.132 | 0.132 |
| Resorcin | — | — | 0.022 |
| Water | ad 100 | ad 100 | ad 100 |

The dye creams V1, E1 and E2 were each mixed in the weight ratio of 1:1 with the following oxidant preparation.

| Oxidant preparation (quantity 100 g) | OX |
|---|---|
| Dipicolinic acid | 0.1 g |
| Sodium pyrophosphate | 0.03 g |
| Turpinal SL (1-hydroxyethan-1,1-diphosphonic acid, 58-61 wt. % active substance) | 1.50 g |
| Texapon N28 (sodium laureth sulfate, min. 26.5 wt. % active substance) | 2.00 g |
| Aerysol 22 (Acrylates/Steareth-20 Methacrylat Copolymer, active substance 29.5-30.5 wt. %) | 0.60 g |
| Hydrogen peroxide (50% hydrous solution) | 6.0 g |
| Sodium hydroxide (45% hydrous solution) | 0.80 g |
| Water (dist.) | ad 100 g |

1.2. Application

Hair strands (buffalo belly hair and Kerlin 7-0 (dark blond)) were measured by colorimetry. The previously produced ready-to-use oxidative dyes (V1+OX, E1+OX, E2+OX) were then each applied to the hair strands (buffalo belly hair and Kerlin 7-0 (dark blond)) and left to work in for a period of 30 minutes. The strands were then rinsed with lukewarm water for one minute and dried in a cold air flow. Each hair strand was then measured by colorimetry again. For each formulation, 5 measured values were obtained and the mean value was determined from said measured values in each case.

1.3. Determination of the Gray Coverage

The uncolored buffalo bellow hair used in the tests was employed as a model for uncolored, grayed human hair. The dark blond hair strands used in the tests (Kerling 7-0) are uncolored, pigmented hair. All the obtained measured values were used to calculate the gray coverage index (GCI) according to the following formula:

$$GAI = \left[1 - \frac{dE(BB - Kerling\,(7-0))}{dE(uncol \cdot BB - Kerling\,(7-0))}\right] \cdot 100$$

dE (BB–Kerling (7-0))=color difference between BB (colored buffalo belly hair) and colored pigmented hair (Kerling (7-0)

dE (uncol BB–Kerling (7-0))=color difference between uncol. BB (uncolored buffalo bellow hair) and colored pigmented hair (Kerling 7-0).

The higher the gray coverage index (GCI), the better the gray coverage.

The following values were obtained:

| | CIE L sample | CIE a sample | CIE b sample | De (BB-K(7-0)) | dE (uncol. BB-K(7-0)) | GCI [%] |
|---|---|---|---|---|---|---|
| uncol. BB | 73.47 | −0.58 | 10.49 | | | |
| V1 + OX on buffalo belly hair | 47.31 | 30.28 | 37.94 | 29.88 | 45.75 | 34.7 |
| V1 + OX on Kerling (7-0) | 30.96 | 14.13 | 18.85 | | | |
| E1 + OX on buffalo belly hair | 43.00 | 23.94 | 29.49 | 20.79 | 46.49 | 55.3 |
| E1 + OX on Kerling (7-0) | 29.75 | 13.78 | 17.11 | | | |
| E2 + OX on buffalo belly hair | 38.23 | 26.69 | 26.36 | 18.33 | 48.30 | 62.1 |
| E2 + OX on Kerling 7-0 | 28.20 | 15.29 | 16.10 | | | |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. Agent for the oxidative dyeing of keratinous fibers, comprising in a cosmetic carrier:
   (A) 1-(2-Hydroxyethyl)-4,5-diaminopyrazole and/or one of the physiologically-tolerated salts thereof;
   (B) 2,6-dihydroxy-3,4-dimethylpyridine; and
   (C) toluene-2,5-diamine and/or one of the physiologically-tolerated salts thereof;
   wherein the weight ratio of (A) to (C) is from about 1.0 to about 8.0.

2. Agent according to claim 1, wherein the agent comprises, relative to a total weight of the agent, (A) from about 0.005 to about 5.0 wt. % of 1-(2-hydroxyethyl)-4,5-diaminopyrazole sulfate.

3. Agent according to claim 1, wherein the agent comprises, relative to a total weight of the agent, (B) from about 0.001 to about 3.5 wt. % of 2,6-dihydroxy-3,4-dimethylpyridine.

4. Agent according to claim 1, wherein the agent comprises, relative to a total weight of the agent, (C) from about 0.005 to about 5.0 wt. % of toluene-2,5-diamine sulfate.

5. Agent according to claim 1, wherein the agent comprises (D) resorcin, 4-chlorresorcin, and/or 2-methylresorcin.

6. Agent according to claim 1, wherein the agent comprises, relative to a total weight of the agent, (D) from about 0.001 to about 0.5 wt. % of resorcin.

7. Agent according to claim 1, wherein the agent comprises, relative to a total weight of the agent, (D) from about 0.003 to about 0.55 wt. % of 2-methylresorcin.

8. Agent according to claim 1, wherein the weight ratio of (A) to (B) is from about 0.7 to about 2.0.

9. Agent according to claim 5, wherein the weight ratio of (A) to (D) is from about 5.0 to about 60.0.

10. Agent according to claim 1, wherein the agent comprises (E) 2-amino-3-hydroxypyridine.

11. Method for the oxidative dyeing of keratinous fibers, the method comprising:
  (i) producing a ready-to-use agent for lightening keratinous fibers by mixing a first component (K1) with a second component (K2);
  (ii) distributing the ready-to-use agent onto the keratinous fibers;
  (iii) leaving the agent on the fibers for a period from 1 to 60 minutes; and
  (iv) washing the agent out of the fibers;
  wherein the first component (K1) is an agent according to claim 1; and
  wherein the second component (K2) is an oxidant preparation, which comprises hydrogen peroxide.

12. Method according to claim 11, wherein the first component (K1) and the second component (K2) are mixed with one another in a weight ratio of (K1)/(K2) from about 0.3 to about 3.0.

13. Agent according to claim 2, wherein the agent comprises from about 0.05 to about 3.0 wt. % of 1-(2-hydroxyethyl)-4,5-diaminopyrazole sulfate.

14. Agent according to claim 3, wherein the agent comprises from about 0.1 to about 1.2 wt. % of 2,6-dihydroxy-3,4-dimethylpyridine.

15. Agent according to claim 4, wherein the agent comprises from about 0.07 to about 0.7 wt. % of toluene-2,5-diamine sulfate.

16. Agent for the oxidative dyeing of keratinous fibers, comprising in a cosmetic carrier:
  (A) from about 0.05 to about 3.0 wt. % of 1-(2-Hydroxyethyl)-4,5-diaminopyrazole and/or one of the physiologically-tolerated salts thereof;
  (B) from about 0.1 to about 1.2 wt. % of 2,6-dihydroxy-3,4-dimethylpyridine; and
  (C) from about 0.07 to about 0.7 wt. % of toluene-2,5-diamine and/or one of the physiologically-tolerated salts thereof; and
  (D) from about 0.001 to about 0.5 wt. % of resorcin, 4-chlorresorcin, and/or 2-methylresorcin;
  wherein all amounts are relative to a total weight of the agent; and
  wherein the weight ratio of (A) to (C) is from about 1.0 to about 8.0.

* * * * *